(12) United States Patent
Green

(10) Patent No.: US 11,844,811 B2
(45) Date of Patent: Dec. 19, 2023

(54) METHODS AND COMPOSITIONS FOR ALLEVIATING RESPIRATORY DYSFUNCTION

(71) Applicant: Shawn J. Green, Bethesda, MD (US)

(72) Inventor: Shawn J. Green, Bethesda, MD (US)

(73) Assignee: MYFITSTRIP LLC, Rockville, MD (US)

(*) Notice: Subject to any disclaimer, the term of this patent is extended or adjusted under 35 U.S.C. 154(b) by 31 days.

(21) Appl. No.: 16/936,036

(22) Filed: Jul. 22, 2020

(65) Prior Publication Data

US 2020/0352986 A1 Nov. 12, 2020

Related U.S. Application Data

(63) Continuation-in-part of application No. 16/416,734, filed on May 20, 2019, now abandoned.

(60) Provisional application No. 62/674,008, filed on May 20, 2018.

(51) Int. Cl.
*A61K 33/00* (2006.01)
*A61K 31/375* (2006.01)
*A61P 31/14* (2006.01)

(52) U.S. Cl.
CPC .......... *A61K 33/00* (2013.01); *A61K 31/375* (2013.01); *A61P 31/14* (2018.01)

(58) Field of Classification Search
None
See application file for complete search history.

(56) References Cited

U.S. PATENT DOCUMENTS

| 8,303,995 B1 | 11/2012 | Bryan et al. |
| 2014/0100277 A1* | 4/2014 | Gray ............ A01N 37/36 514/557 |
| 2015/0038584 A1 | 2/2015 | Fridman et al. |
| 2015/0306258 A1 | 10/2015 | Ferrell et al. |

FOREIGN PATENT DOCUMENTS

WO 2016/096751 A1 6/2016

OTHER PUBLICATIONS

Beitler et al, "Preventing ARDS", Chest, 2014, 146(4) pp. 1102-1113 (Year: 2014).*
Nature News ([retrieved from on-line website: https://www.nature.com/articles/d41586-021-00728-2, 2021]). (Year: 2021).*

(Continued)

*Primary Examiner* — Kyung S Chang
(74) *Attorney, Agent, or Firm* — DUANE MORRIS LLP

(57) ABSTRACT

Compositions, methods of manufacturing compositions, methods of protecting against respiratory problems including coronavirus and coronavirus-associated severe acute respiratory syndrome (SARS) in humans and animals, are provided. Compositions comprising inorganic nitrate used for improving nitric oxide levels, improving health and/or reducing symptoms of SARS are provided. The compositions and methods are applicable for subjects experiencing SARS, and for protecting non-infected subjects against SARS. Compositions and methods for improving nitric oxide levels in a subject disclosed herein comprise administration of compositions comprising inorganic nitrate such as potassium nitrate or sodium nitrate optionally combined with ascorbate.

5 Claims, 4 Drawing Sheets

(56) References Cited

OTHER PUBLICATIONS

Hord et al., "Food sources of nitrates and nitrites: the physiologic context for potential health benefits,", Am J Chlin Nutr 2009: 90: 1-10. (Year: 2009).*

Mascarenhas, "Explained: Can nitric oxide fight coronavirus? A nasal spray, and evidence so far", Indianexpress, 2021, pp. 1-6 ([see retrieved from on-line website: https://indianexpress.com/article/explained/coronavirus-nitric-oxide-nasal-spray-7286590/, 2022])(Year: 2021).*

Kirch et al., "Acute respiratory distress syndrome after chemotherapy for lung metastases from non-seminomatous germ-cell tumors", Support Care Center (2003) 11: pp. 575-580. (Year: 2003).*

R.S. Baliga et al., "Dietary nitrate ameliorates pulmonary hypertension: cytoprotective role for endothelial nitric oxide synthase and xanthine oxidoreductase", Published in Final Edited Form as Circulation, 125 (23): 2922-2932, Jun. 12, 2012.

\* cited by examiner

METHODS AND COMPOSITIONS FOR ALLEVIATING RESPIRATORY DYSFUNCTION

CROSS-REFERENCE TO RELATED PATENT APPLICATIONS

This application is a continuation-in-part application of U.S. patent application Ser. No. 16/416,734 filed on May 20, 2019 which claims priority to U.S. Provisional Patent Application Ser. No. 62/674,008, filed on May 20, 2018, the contents of which are incorporated by reference in their entireties for all purposes.

TECHNICAL FIELD

Provided herein are methods and compositions for treating, preventing and/or managing respiratory dysfunction, such as symptoms of severe acute respiratory syndrome (SARS) and acute respiratory distress symptoms (ARDS), in subjects that present nitric oxide deficiencies. The present invention further relates to methods for treating and preventing unwanted symptoms of coronavirus infection and coronavirus-associated SARS infection in humans and animals. The health benefits of consuming the compositions of the invention include, restoring endothelium function, preventing thrombotic events, and increasing direct anti-viral activity. The embodiments herein enable the improvement of health conditions, in particular, those related to the protection of individuals against SARS when exposed to individuals with clinical presentation of SARS, and for alleviating SARS complications of infected individuals by maintaining endothelium function, preventing or reducing thrombotic events, and preventing or reducing viral infection. Embodiments of the disclosed subject matter also improve health outcomes in subjects with clinical presentation of ARDS by restoring nitric oxide mediated antimicrobial and antitumor activity in nitric oxide deficient subjects. The invention provided herein prevents and treats viral, bacterial, fungal infections as well as cancer, comprising the ingestion of nitrate-ascorbate on an as-needed basis, calculated for example, by an assessing nitric oxide bioavailability as determined by salivary nitrite or nitrite/nitrate levels.

BACKGROUND OF THE INVENTION

An active entero-salivary circulation in subjects provides a continuous flow of nitrate into the mouth where it is rapidly reduced to nitrite by bacteria on the tongue. In the mouth bacteria rapidly reduce nitrates to nitrites. Once swallowed the acid conditions of the stomach protonate the nitrite to form nitrous acid (Equation 1). The nitrous acid in turn dissociates to form oxides of nitrogen as shown below (Equations 2-4).

$$NO_2^- + H^+ = HNO_2 \qquad \text{Equation 1:}$$

$$2HNO_2 = H_2O + N_2O_3 \qquad \text{Equation 2:}$$

$$N_2O_3 = NO + NO_2 \qquad \text{Equation 3:}$$

$$N_2O_3 + C_2H_8O_6 = 2NO + H_2O + C_6H_6O_6 \qquad \text{Equation 4:}$$

Endogenous and dietary nitrate is actively concentrated by salivary glands to more than ten times the concentration in plasma and secreted in saliva. Thus, the saliva provides a continuous source of nitrate to the upper gastrointestinal tract. Oral conversion of nitrate to nitrite is rapid and is restricted to the surface of the tongue in humans and animals.

The function of the entero-salivary circulation of nitrate is not completely clear but it may well be that gastric acid by itself is not always sufficient to destroy many ingested micro-organisms and that the primary role of salivary nitrate secretion and conversion to nitrite is as a precursor for nitrogen oxides in the lumen of the stomach which will kill swallowed micro-organisms.

Prior art discussions of related technology do not provide or enable effective measures by which physiological levels of nitrogen oxides may be elevated or by which they may be utilized to combat infection, cancer or alleviate respiratory distress.

WO 95/22335 disclosed a pharmaceutical composition comprising a pharmaceutically acceptable source of nitrites and a pharmaceutically acceptable acidifying agent for the direct treatment of disease by topical application.

U.S. Pat. No. 4,595,591 reveals a composition comprising an aqueous solution of nitric acid and nitrous acid at a pH below 1, preferably with an organic acid and copper and cadmium ions for the treatment of superficial lesion of the skin, for example tumorous growths.

U.S. Pat. No. 5,648,101 provides a vasoactive composition comprising NO adapted for delivery to a body site by means of a cream or ointment. The NO is generated from an admixture of ferrous sulphate, an organic acid and an inorganic nitrite and caused to be reactive in the presence of moisture adjacent or at the site.

WO 96/02268 reveals the inhibition of a virus by nitric oxide derived from a complex unstable organic molecule to release NO and $NO_2$ moieties immediately adjacent to the environment of use.

WO 93/25213 reveals a composition comprising nitrous oxide contained in a dermatological composition comprising as an essential feature a fatty acid or a lower alkyl ester thereof, pH values, particularly at the environment of use.

All of the above cited prior art references are single formulations which are admixed well prior to application to the environment of use so that NO and $NO_2$ all escape prior to use and hence have a very limited utility.

Further, U.S. Pat. No. 6,709,681 B1 discloses acidified nitrite as antimicrobial as a topical agent.

In like fashion, U.S. Pat. No. 9,925,206 B2 discloses a composition comprising a therapeutically effective amount of acidified nitrite NO2, an iron chelator agent, and an antibiotic agent, wherein the iron chelator agent is EDTA or DPTA.

What is needed are convenient and effective measures by which to improve nitric oxide levels and availability in humans and animals. Compositions comprising potassium nitrate, sodium nitrate, or an inorganic nitrate from a plant-based source in the absence of a nitrite salt or acidified nitrite and an acidifying agent for oral consumption for preventing and treating conditions of respiratory distress, such as that related to SARS, ARDS, infections and cancer are also desired.

Furthermore, what is needed are convenient and routine measures to enable the intermittent daily consumption of nitrate salt in the absence of nitrite to achieve desired concentrations based on salivary nitrite to prevent and treat respiratory dysfunction, SARS, ARDS, cancer, nitric oxide deficiency disorders and symptoms.

SUMMARY OF THE INVENTION

Disclosed herein are methods and compositions for treating, preventing, alleviating and managing nitric oxide deficiencies, such deficiencies may be related to respiratory distress including but not limited to, acute respiratory distress syndrome (ARDS), Severe Acute Respiratory Syndrome (SARS). Respiratory distress may also be associated with infectious diseases, metastatic cancer and other nitric oxide deficient-related complications.

In an embodiment, the present disclosure relates to compositions and methods that are effective for the prevention, treatment and/or alleviation of complications related to SARS and ARDS, including for example, symptoms related to nitric oxide deficiencies, infectious diseases and cancer.

In an embodiment, the present disclosure relates to the safeguard of front-line health workers that are exposed to infectious disease, such as coronavirus and influenza-infected patients.

Disclosed herein are compositions and methods of protecting against and treating SARS. There exists a clear need for a low cost, orally self-administrated prophylactic with day-to-day conveniences including for example, the ability to easily self-monitor antiviral protective nitric oxide levels. In an embodiment, the compositions of the invention are non-invasive. Currently available antivirals are expensive, require injection with health care support, and patients are usually unable to monitor the effects or efficacy except for clinical presentation, such as viral burden. In contrast, the compositions of the present invention are novel and effective easy to administer and enable the alleviation of respiratory dysfunction associated with, or resulting from, SARS and ARDS, as well as related to pathogenic infectious disease (including coronavirus infection) and cancerous conditions.

As disclosed herein, the present invention overcomes the limitations and problems of the prior art in that it comprises (1) methods of naturally generating and prolonging the efficacy of a protective nitric oxide dose by an single oral dose (with optional intermittent dosing) optionally based on upon non-invasive, periodic rapid self-saliva testing and/or (2) the use of defined nitrate or nitrate-ascorbate drinking water, lozenge, chewable, or capsule for the treatment, prevention and/or managing nitric oxide deficiencies associated with SARS or ARDS, specifically, wherein a subject is diagnosed with ARDS or SARS, or wherein a subject is exposed to an individual with ARDS or SARS. The symptoms of such subjects may include difficulty breathing, low oxygenation, thrombotic events, flu-like symptoms, sore throat or fever.

DETAILED DESCRIPTION OF THE INVENTION

Figure 1:
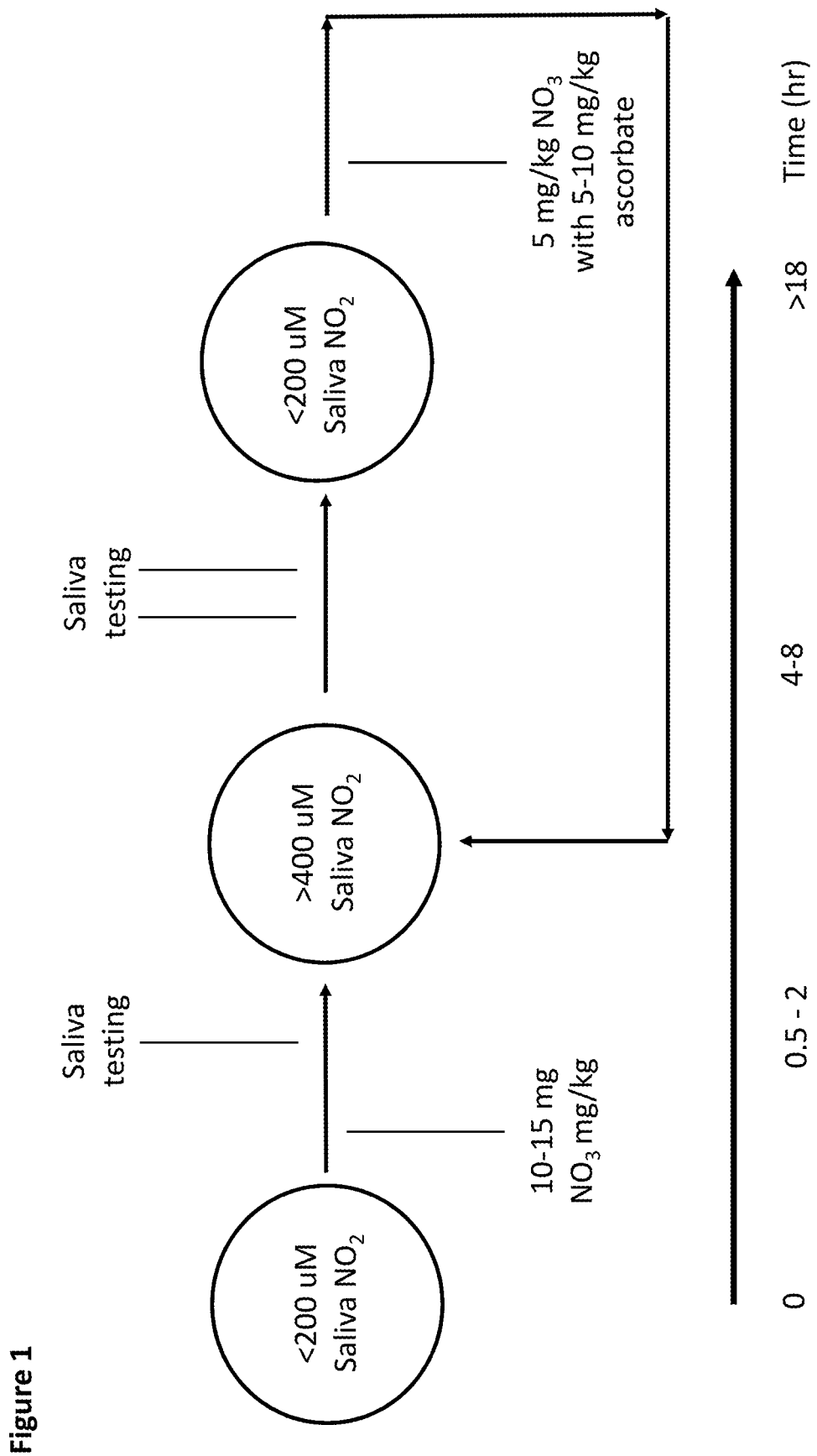
FIG. 1. A schematic of a method to increase and sustain nitric oxide bioavailability and anti-microbial activity, lessen SARS and ARDS conditions, and treat symptoms or conditions of nitric oxide deficiencies and nitric oxide deficient-related diseases. As illustrated, the timeline, dosing and frequency of testing is predicated on a number of independent and dependent factors that may be instructive and guidance dosing, such as monitoring salivary nitrite or nitrite/nitrate levels, which will vary based on gender, weight, lifestyle, and dietary patterns based on a specific individual's needs. This schematic is illustrative of a variation of a method to be implemented.
Figure 2:
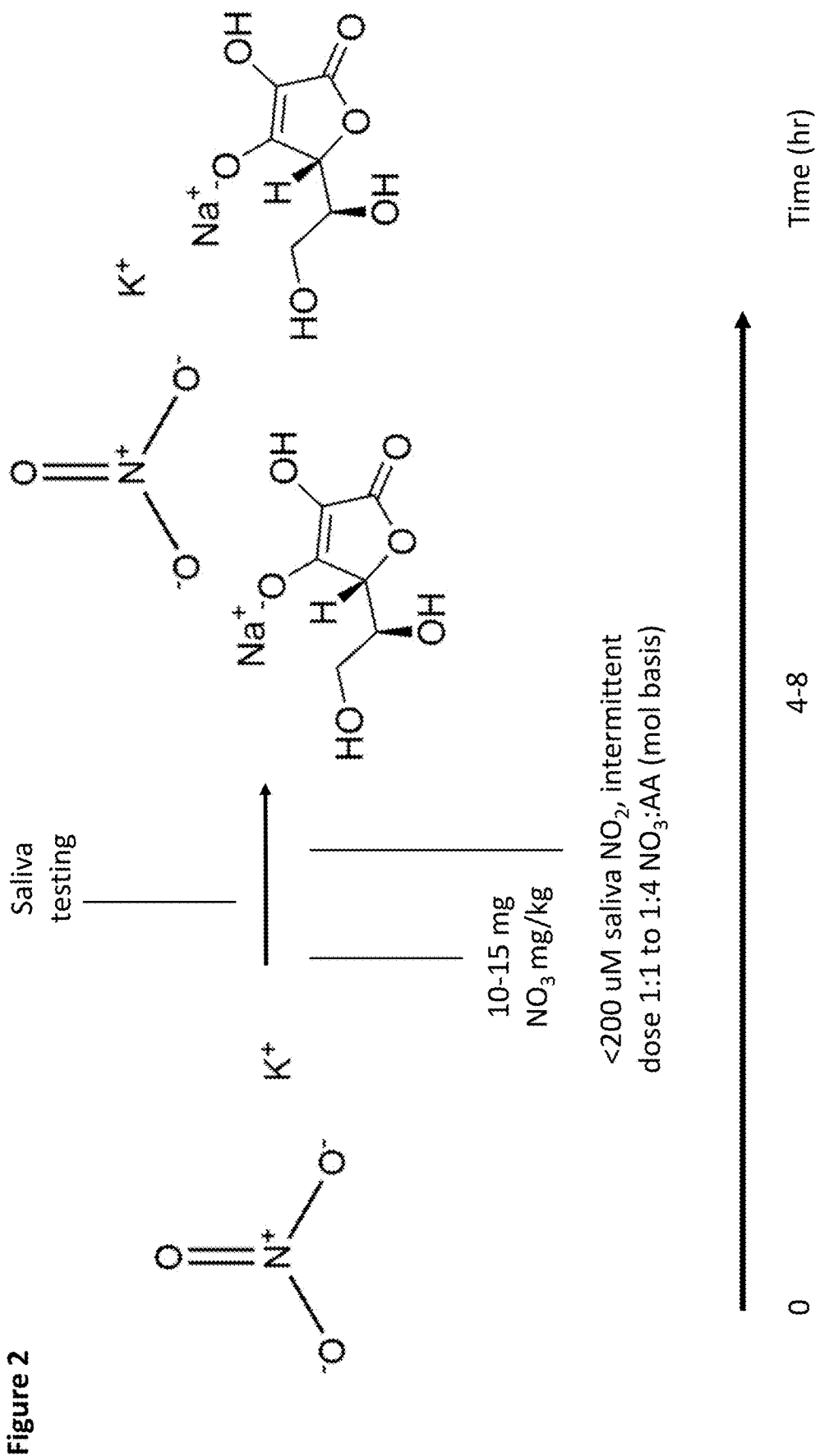
FIG. 2. The schematic of the ingredients and example of a ratio of the ingredient formula for initial dosing and intermittent dosing. This schematic is illustrative which will vary based on the salivary monitoring, gender, weight.

The following detailed description is explanatory and is intended to provide further explanation of the present disclosure described herein. Other advantages, and novel features will be readily apparent to those skilled in the art from the following detailed description of the present disclosure.

In an embodiment, provided herein are novel methods for improving health, including alleviating nitric oxide deficient-related complications comprising the consumption inorganic nitrate compositions by a subject in need thereof. In an embodiment, consumption of the nitrate-rich composition results in bio-convertible to nitric oxide achieved independently of exogenously added sources of nitrite and acidified nitrite admixed. In an embodiment, the methods and compositions allow a subject to sustain antimicrobial and antitumor activity. For example, after initial dosing, the methods herein enable intermittent dosing to extend elevated nitric oxide levels for preventing, reducing, or treating severe acute respiratory syndrome and acute respiratory syndrome. Compositions and methods of the invention may be used to alleviate respiratory dysfunction associated with any cause, including but not limited to, complications caused by coronaviruses such as severe acute respiratory syndrome (SARS) caused by SARS-CoV, and COVID-19 caused by SARS-CoV-2. Such compositions and methods may be useful for the prevention of influenza and coronavirus related infections, along with other viral and pathogenic infections, ie, fungal, bacterial and mycobacterial, as well as metastatic cancer including lung cancer.

In another aspect of the invention, the composition of the invention may be utilized to inhibit the growth of infectious organisms, including but not limited to, streptococci and lactobacilli, the causative agents of caries and tooth decay. As known to those skilled in the art, high counts of *mutans* streptococci and/or lactobacilli indicate a high caries risk status. If protective factors cannot take effect, carious lesions develop. As demonstrated herein, the compositions are effective in reducing and/or eliminating cariogenic bacteria.

In another aspect of the invention, the compositions and methods of the invention may be utilized to inhibit the growth of tumor and pre-cancerous growth in subjects. The use of compositions in this capacity may be beneficial for a variety of cancers including but not limited to, colon, bladder, stomach, as well as vascularized tumors found for example, in the lung, brain, bone, liver, pancreas, among other organs and glands. Though not wishing to be bound by the following theory, it is known that nitrate and nitrite ingestion contribute to cancer through the formation of nitrosamines. For decades, nitrosamine has been deemed carcinogenic by regulatory agencies based on preclinical studies. Acidified nitrite has been reported to inhibit bacterial and transformed cell growth in vitro; but such nitrite salts have not been considered in vivo. Surprisingly, the present invention addresses this issue by showing that nitrate alone, not nitrite, acidified nitrite or admixed, when ingested can be used for the alleviation of cancer and prevention of tumor formation or metastasis. This invention claims the use of nitrate as anti-tumorgenic and can prevent the growth of transformed cells. The findings demonstrated herein show that the present methods and compositions are novel, uniquely non-obvious, and unexpected given that nitrate and nitrite are labeled carcinogens and would not be consider as a cancer treatment modality based on the evidence thus far, but instead would be promoters of cancer.

Effective dosages and schedules for determining the intake of the compositions herein may be determined empirically, and making such determinations is within the skill of those in the art. The dosage ranges for the administration of the supplements are those large enough to produce the desired effect in which the nitric oxide levels are modified to acceptable or desirable levels. The dosage should not be so large as to cause adverse side effects. Generally, the dosage will vary with the age, condition, sex and extent of the nitric oxide levels desired, frequency of administration, or whether other drugs are included in the regimen, and can be determined by one of skill in the art.

Clinical studies have shown that 5-7 mM (310-434 mg/L/day) nitrate is sufficient to reduce systolic blood pressure in hypertensives by 4-11 mmHg. In the case of the DASH diet, with 4-6 serving of nitrate-rich leafy greens the NO3 may exceed 1000 mg/L/day. Despite a number of clinical and scientific papers discussing nitrates and their impact on human and animal health, the compositions and methods as provided herein have never been disclosed with respect to the use of supplements to alleviate nitric oxide deficiencies-related to subjects experiencing respiratory difficulties such as those diagnosed with SARS, ARDS, infectious disease or those diagnosed with lung cancer. One unique benefit of this invention is that the consumer or user can both measure the nitrate prior to and post consumption with a simple Griess reagent test strip and make adjustments to the amount of nitrate based on consumer's levels. In an embodiment of this invention, the level of plasma activation is determined by a semiquantitative colorimetric nitrite or nitrite/nitrate test strip.

Following intake of the compositions disclosed herein, the efficacy of the intake may be assessed in various ways well known to the skilled practitioner. For example, one of ordinary skill in the art will understand that the composition as described herein is efficacious in treating or inhibiting symptoms associated with nitric oxide deficiencies. Furthermore, nitric oxide levels can be measured by methods that are known in the art, for example, using a saliva test strip to detect the bioconversion of nitrate to nitrite in the oral cavity, a necessary and critical step.

Methods and compositions for preventing or alleviating respiratory distress in a subject comprising administrating to the subject a composition comprising symptom-preventing or symptom-reducing dose amount of potassium nitrate, sodium nitrate, or inorganic nitrate (optionally derived from a vegetable source) separately, simultaneously or sequentially with ascorbate, and monitoring the subject for improvement in respiratory conditions are provided. In certain embodiments, plasma activated water (PAW) may comprise a source of nitrate. The symptoms of respiratory distress may comprise difficulty in breathing, low oxygenation, thrombotic events, flu-like symptoms, sore throat, fever, coughing, X-ray detected pulmonary infiltrates, vasculitis, or endotheliitis.

In certain embodiments the symptom-preventing or symptom-reducing dose amount of either potassium nitrate, sodium nitrate, or nitrate salt is from about 1 to 50 mg/kg/day, 1 to about 40 mg/kg/day, 1 to about 30 mg/kg/day, 1 to about 30 mg/kg/day, 5 to about 20 mg/kg/day, 5 to about 15 mg/kg/day, 5 to about 10 mg/kg/day. The symptom-preventing or symptom-reducing dose amount of inorganic nitrate derived from a vegetable source comprises from about 25% to 50% nitrate weight basis (mg nitrate/g dry weight of vegetable powder extract).

In an embodiment, plasma activated water is diluted to achieve an inorganic nitrate preventative dose or boiled to remove the liquid phase and the resultant water-soluble solute reconstituted to achieve an effective amount of inorganic nitrate to exceed 5 mM. In certain embodiments, the preventative effective amount of ascorbate in combination with a nitrate source is from 0 to about 15 mg/kg/day.

In certain embodiments, the oral administration of the compositions described herein increase salivary nitrite or salivary nitrite/nitrite within approximately 90 minutes after consumption by the subject. Salivary nitrite or nitrite/nitrate may be monitored with a dry-based Griess reagent test strip to determine the subsequent administration of nitrate, nitrate-ascorbate, or post-nitrate ascorbate dose. In certain embodiments, subjects may receive intermittent daily dosing of two, or three daily dosing per day to sustain >300 uM salivary nitrite throughout the day. The subject may administer a preventative effective dose and a second or intermittent dose if subsequent salivary nitrite drops below <200 uM; and a second dose may be administered to sustain >300 uM salivary nitrite levels. The second daily dose may be administered within 4-10 hours of the initial dose.

In an embodiment, the compositions of the invention may be water-soluble and can be administered in the form of a capsule, tablet, lozenge, suspension, or dissolved in a water-based drink.

Provided herein are methods for enhancing nitric oxide bioavailability in a subject with detectible nitric oxide deficiencies and/or with clinically presented symptoms of acute respiratory distress syndrome (ARDS), or Severe Acute Respiratory Syndrome (SARS), wherein the subject is administrated a symptom-preventing or symptom-reducing dose amount potassium nitrate, sodium nitrate, nitrate salt, or inorganic nitrate (optionally derived from a vegetable source) separately, simultaneously, or sequentially with ascorbate. In embodiment, plasma-activated water (PAW) is administered for improving nitric oxide bioavailability in a subject.

Provided herein are methods for enhancing nitric oxide bioavailability in individuals such as health care providers and front line personnel working with subjects suffering from infections, such as those suffering from SARS CoV-2 infection, and who may or may not have clinical presentation of acute respiratory distress syndrome (ARDS), Severe Acute Respiratory Syndrome (SARS); wherein the subject is administrated a symptom-preventing or symptom-reducing dose amount potassium nitrate, sodium nitrate, nitrate salt, or inorganic nitrate (optionally derived from a vegetable source) separately, simultaneously, or sequentially with ascorbate. In embodiment, plasma-activated water (PAW) is administered for improving nitric oxide bioavailability in a subject. Symptoms may include, but are not limited to, difficulty in breathing, low oxygenation, thrombotic events, flu-like symptoms, sore throat, fever, coughing, X-ray detected pulmonary infiltrates, vasculitis, or endotheliitis. In certain embodiments, the subject may clinically present or be exposed to individuals that may present one or a combination of the symptoms to include acute respiratory distress syndrome (ARDS), Severe Acute Respiratory Syndrome (SARS) that results from metastatic lung cancer or infections including bacterial, viral, parasitic, or fungal. In an embodiment, the symptom-preventing or symptom-reducing dose amount of either potassium nitrate or sodium nitrate is from about 5 to about 15 mg/kg/day. In another embodiment, the symptom-preventing or symptom-reducing dose amount of inorganic nitrate derived from a vegetable source is from about 25% to 50% nitrate weight basis (mg nitrate/g dry weight of vegetable powder extract). In certain embodiments, the plasma activated water may be diluted to achieve an inorganic nitrate symptom-preventing or symptom-reducing dose, or boiled to remove the liquid phase and the resultant water-soluble solute reconstituted to achieve a preventative effective amount of inorganic nitrate to exceed 5 mM. In certain embodiments, the amount of ascorbate administered in the absence of the nitrate source is from 0 to about 15 mg/kg/day. The compositions may be water-soluble and may be administered in the form of a capsule, tablet, lozenge, suspension, or dissolved in a water-based drink.

In an embodiment, the compositions and methods of the invention are useful for treating subjects experiencing respiratory distress, wherein the respiratory distress is associated with influenza, coronavirus infection, SARS-CoV-1, SARS-CoV-2, MERS, or other respiratory viruses or respiratory diseases causing acute respiratory distress syndrome, including, but not limited to, non-coronavirus, tuberculous or non-tuberculous *Mycobacterium*. Respiratory distress may also be caused by bacteria, including, but not limited to, *Streptococcus pneumoniae, Haemophilus influenzae*, or fungus, including but not limited, to *Aspergillosis*, or cancer (i.e. lung cancer), including, but not limited, to metastatic melanoma, adenocarcinoma, squamous cell carcinoma. In certain embodiments, respiratory distress may be associated with acute respiratory distress syndrome (ARDS), Severe Acute Respiratory Syndrome (SARS), chronic obstructive pulmonary disease (COPD), Kawasaki Disease, tuberculosis, cystic fibrosis, pulmonary hypertension, allergies, smoking cessation, or lung disease.

Variations contemplated in administering the subject composition to humans or other animals include, but are not limited to, providing as a single dose or as other multiple part dosages.

The following examples are given to illustrate exemplary embodiments of the present disclosure. It should be understood, however, that the present disclosure is not to be limited to the specific conditions or details described in these examples. Examples are provided below to facilitate a more complete understanding of the invention. The following examples illustrate the exemplary modes of making and practicing the invention.

EXAMPLES

Example 1

Elevating and Extending Nitric Oxide Bioavailability with Intermittent Ascorbate and/or Low Dose Dietary Inorganic Nitrate-Ascorbate As shown below in Table 1, salivary nitrite, a necessary intermediate in nitric oxide formation, is elevated with ingestion of potassium nitrate. Bioavailability is boosted and extended with intermittent ascorbate or low dose nitrate-ascorbate consumption.

TABLE 1A subject 1: male, 48 yrs, 205 lb, active

| Time | Salivary $NO_2$ (uM) | Dosing |
|---|---|---|
| 7:45AM | 20 uM | |
| 8:00 | | 500 $KNO_3$ mg dose (5 mg/Kg) |
| 9:00 | 400 uM | |
| 11:00 | 220 uM | |
| 11:40 | 110 uM | |
| 1:00PM | 120 uM | |
| 2:00 | 110 uM | |
| 2:45 | <20 uM | |
| 3:00 | | 1,000 mg ascorbate (10 mg/Kg) |
| 3:30 | 140 uM | |
| 4:00 | 200 uM | |
| 6:00 | <200 uM | |

TABLE 1B subject 2: male, 57 yrs, slightly hypertensive, 189 lb, physically active

| Time | Salivary $NO_2$ (uM) | Dosing |
|---|---|---|
| 9:45AM | <20 uM | |
| 10:00 | | 1,000 $KNO_3$ mg dose (12 mgNO3/Kg) |
| 10:30 | 200 uM | |
| 11:00 | 435 uM | |
| 1:00PM | <435 uM | |
| 3:00 | 220 uM | |
| 4:00 | 110 uM | |
| 5:45 | 20 uM | |
| 6:00 | | 50 mg $KNO_3$ + 500 mg ascorbate (60 mg NO3/kg) |
| 9:30 | >435 uM | |
| 10:00 | 435 uM | |
| 11:00 | >220 uM | |
| 7:00AM | >110 uM | |

This example is the first demonstration that total body bioavailability of nitric oxide as measured by the surrogate marker, salivary nitrite, can be extended in the absence of addition dietary nitrate with the intermittent consumption of ascorbate or elevated and extended with low dose of nitrate-ascorbate.

Example 2

Nitrate-Rich Plasma Activated Water Inhibits *S. mutans* in the Oral Cavity Post Gargling Assessment of *S. mutans* and *Lactobacillus* spp. colonization was assessed post gargling for 2 min with repeated rinses (and subsequently swallowed) purified water or purified water sprayed across plasma arc (Example 1). After 2 hrs, saliva samples were taken both group and the CRT test was used.

The CRT bacteria test from Ivoclar Vivadent enables the simultaneous determination of the *S. mutans* and *Lactobacillus* spp. counts in saliva by means of selective agars. The blue mitis-salivarius-agar with bacitracin was used to detect *mutans* streptococci, while the light culture medium, Rogosa agar, was used to evaluate *Lactobacillus*. Foils protected the agars from drying out and contamination. The deep indentation in the carriers prevented the culture media from slipping out.

The agar plates were incubated at 37° C. for 2 days in a CO2 atmosphere (CRT incubator), after added with a tablet of NaHCO3 to stimulate bacterial growth, following which the total count was performed. The NaHCO3 tablet placed in the test vial releases CO2 when it comes into contact with moisture. This creates favorable conditions for bacterial growth.

S. mutans occurred as small blue colonies with a diameter of <1 mm on the blue agar, while Lactobacillus spp. were detected as white colonies on the transparent agar. The comparison with the corresponding pictures in the model chart permitted the assessment of the caries risk. In this context, counts higher than 105 CFU of S. mutans and/or Lactobacillus per milliliter of saliva indicating a high/lower risk for dental caries.

The bacteria count from the purified water was too numerous to count, whereas 2-4 colonies were detected post dietary plasma activated water treatment.

This example is the first demonstration that plasma activated water exhibits antibacteria activity in the mouth as shown by the reduction of the caries promoting bacteria.

Example 3

Effects of Consuming Nitrite-Ascorbate on Metastatic Lung Tumor Growth

Figure 3:
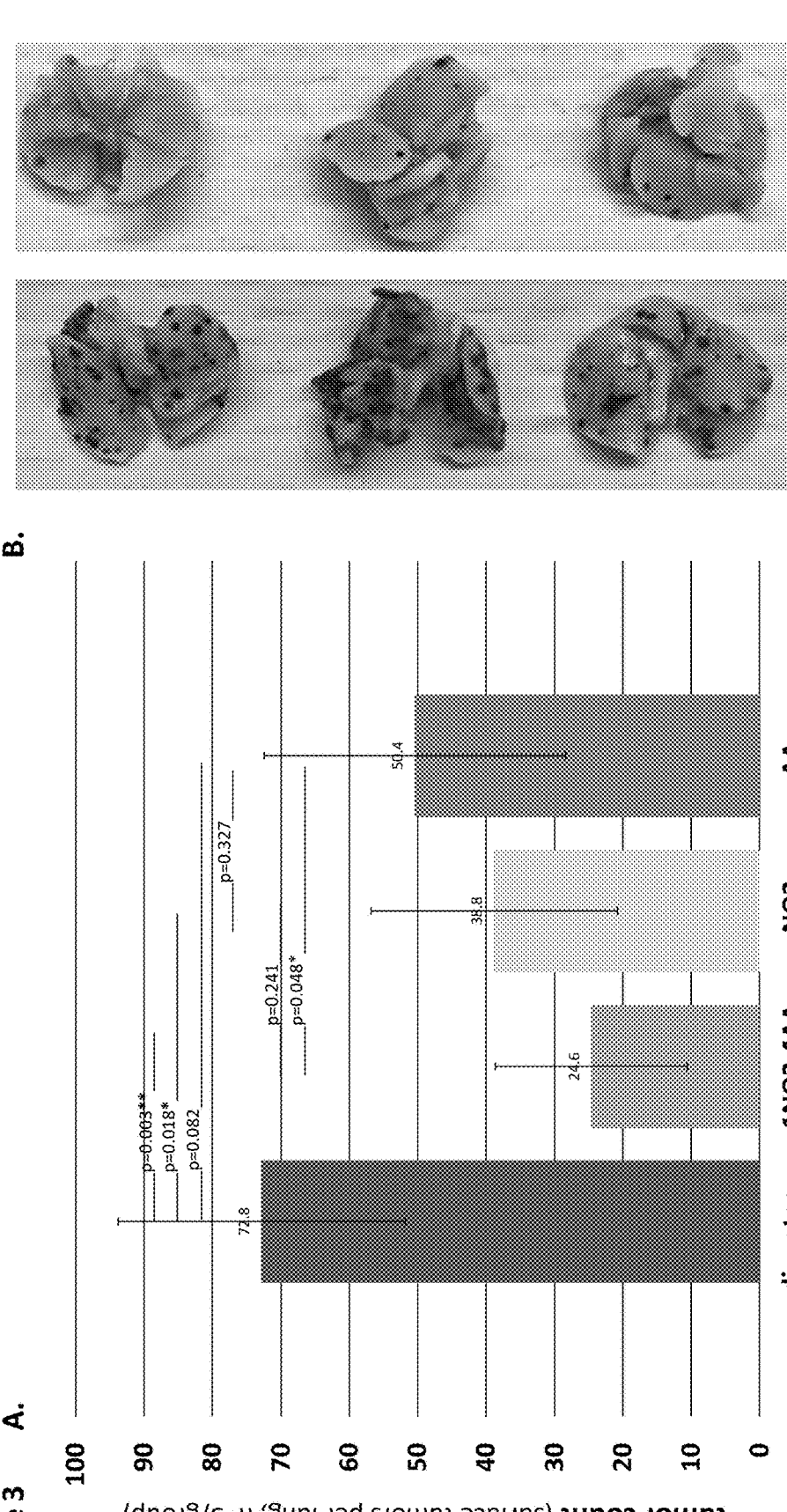
FIG. 3. Mice received drinking water containing 65 mg/L nitrite in the presence of ascorbate at a ratio of 1:4; nitrite: ascorbate, on mole basis. Mice were injected via the tail vein with $10^6$ B16-F10 melanoma cell and placed on ad lib drinking water containing distilled, acidified water (pH 3) (di-water), nitrite-ascorbate (NO2:AA), nitrite (NO2), or ascorbate (AA). After 14 days, animals exsanguinated, lungs removed, fixed, and tumors counts.

As shown in FIG. 3, composition comprising nitrites reduce metastatic tumor growth by approximately 70%. Mice received drinking water containing 65 mg/L nitrite in the presence of ascorbate at a ratio of 1:4; nitrite:ascorbate, on mole basis. Mice were injected via the tail vein with $10^6$ B16-F10 melanoma cell and placed on ad lib drinking water containing distilled, acidified water (pH 3) (di-water), nitrite-ascorbate (NO2:AA), nitrite (NO2), or ascorbate (AA). After 14 days, animals exsanguinated, lungs removed, fixed, and tumors counts. In human, dietary nitrate is reduced to nitrite, a necessary step to generate nitric oxide, by the natural microflora in the mouth. In germfree mice, nitrite was provided in lieu of nitrate to bypass this step because nitrate reducing bacteria was limited.

This example is the first demonstration that a dietary nitrate/nitrite composition reduces and/or prevents the establishment of tumors in lungs.

Example 4

Effects of Ascorbate on Extending the Release of NO Gas

Figure 4:
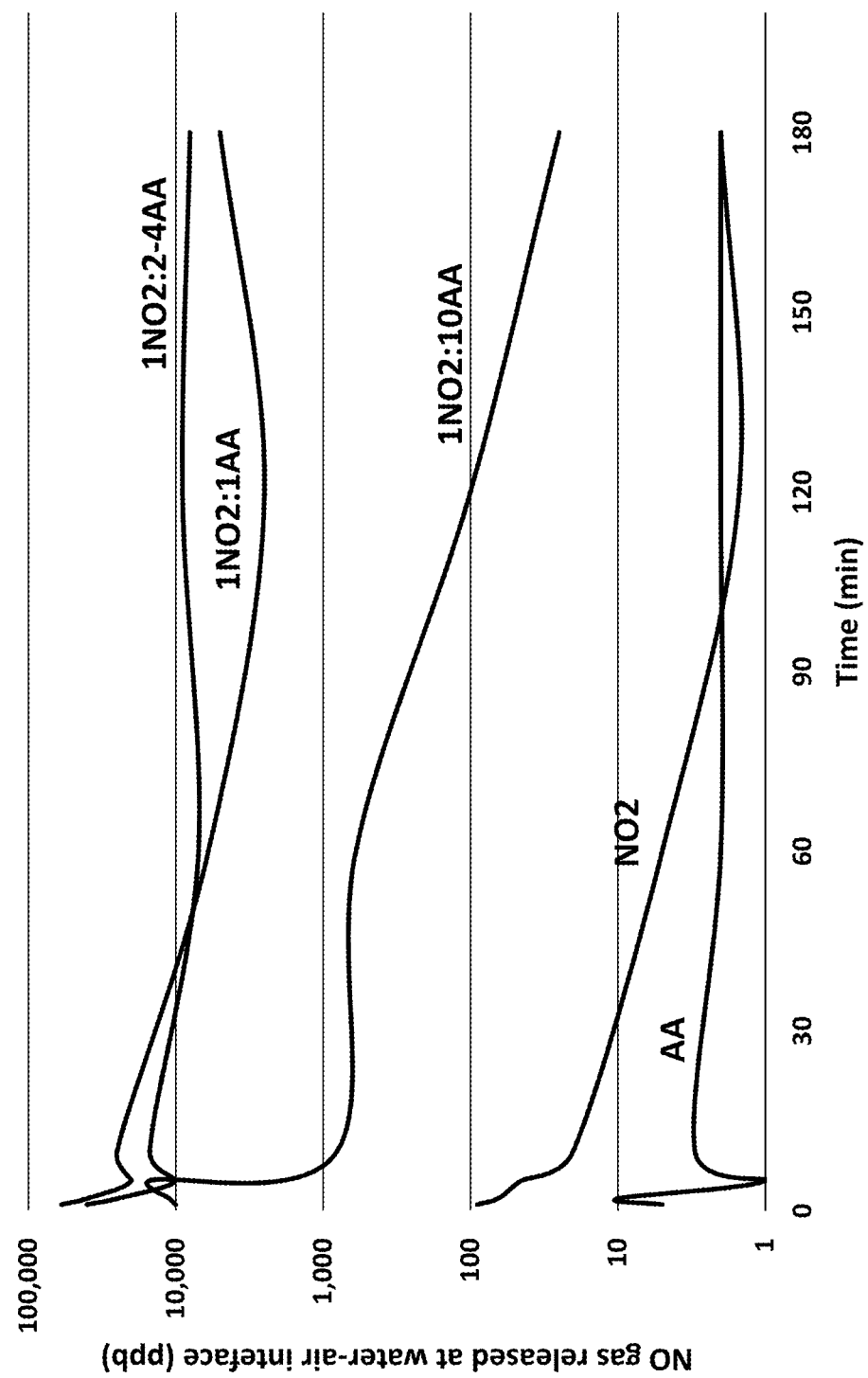
FIG. 4. Measurement of nitric oxide gas (ppb) at the water-air interface in an open system of nitrite water treated with ascorbate. Values represent the ratio of nitrite-to-ascorbate on the mol basis. Gas was continuous monitored for 2 hrs as shown in FIG. 4 (Example 4).

As shown in FIG. 4, nitric oxide gas (ppb) at the water-air interface is enhanced in an open system of nitrite water treated with ascorbate. Values represent the ratio of nitrite-to-ascorbate on the mol basis. A ratio of 1 sodium nitrite to 2 to 4 ascorbate is optimal for elevating and extending nitric oxide release in an open system, whereas if the ascorbate exceeds a ratio of 4 or is less than 1 of nitrite: ascorbate is not effective. Gas was continuous monitored for 2 hours as shown in FIG. 4.

Example 5

Prevention of Covid-19 for Healthcare Providers and Front Line Personnel

Evaluate healthcare providers and front line personnel caring for patients positive with SARS-CoV-2 infection. Providers randomized either in observational group or in dietary NOx group under an blinded, masked label. For observational group a SARS-CoV-2 rt-PCR will be performed if symptoms arise. For dietary NO group, providers will self-administer NO capsules daily and measured for surrogate marker, NO2, with NO saliva self-test strip (2 min., non-invasive self-test) 3 times daily to ensure elevated NO bioavailability. A SARS-CoV-2 rt-PCR will be performed if symptoms arise. For Safety oxygenation levels will be monitored via a non-invasive CO-oximeter. Primary outcome: SARS-CoV-2-rt-PCR at 14 day and IgM/IgG at 21 days with continued administration for 30 days with a reassessment of whole blood anti-Covid-19 Abs.

Example 6

Treatment of Covid-19 Patients

Examine dietary nitric oxide formula as a supportive measure in treating patients infected with SARS-CoV-2: efficacy of dietary nitric oxide formula for pulmonary complications associated with coronavirus and direct anti-viral activity. SARS-CoV-2 rt-PCR positive patients with SARS symptoms would be randomized either in control group or in dietary NOx group under an blinded, masked label. For control group institutional care will be delivered. Dietary NO group, in addition to standard care, the patients will receive NOx capsules daily and measured for surrogate marker, NO2, with NO saliva self-test strip (2 min., non-invasive self-test) or NO2/NO2 serum daily to ensure elevated NO bioavailability for 14 days from enrollment. For Safety oxygenation levels will be monitored via a non-invasive CO-oximeter. Primary outcome: SARS-CoV-2-rt-PCR at 14 day with continued administration for 30 days.

Having described the invention with reference to a particular method and composition it will be apparent to those of skill in the art that it is not intended that the invention be limited by such illustrative embodiments, and that modifications can be made without departing from the scope or spirit of the invention. It is intended that all such obvious modifications and variations be included within the scope of the present invention as defined in the appended claims. The claims are meant to cover the claimed components and steps in which is effective to meet the objectives there intended, unless the context specifically indicates to the contrary.

The invention claimed is:

1. A method for enhancing nitric oxide bioavailability in a subject in need thereof, wherein the subject has detectible nitric oxide deficiencies associated with symptoms of acute respiratory distress syndrome (ARDS), or Severe Acute Respiratory Syndrome (SARS), and wherein the symptoms result from metastatic lung cancer or viral infections;
  wherein the subject is administrated a composition comprising a symptom-reducing dose amount potassium nitrate, wherein the potassium nitrate, is administered with ascorbate,
  wherein the potassium nitrate and ascorbate is present in a weight ratio of 1 to 2,
  and wherein the composition is water-soluble and is administered in the form of a capsule, tablet, lozenge, or chewable.

2. The method of claim 1, wherein the detectible nitric oxide deficiency is determined by salivary nitrite or nitrite/nitrate measurement with nitrite level <20 uM.

3. The method of claim 1, wherein the symptoms comprise difficulty in breathing, low oxygenation, thrombotic events, sore throat, fever, coughing, X-ray detected pulmonary infiltrates, vasculitis, or endothelitis.

4. The method of claim 1, wherein the symptom-reducing dose amount of potassium nitrate is from about 1 to 50 mg/kg/day, 1 to about 40 mg/kg/day, 1 to about 30 mg/kg/day, 1 to about 30 mg/kg/day, 5 to about 20 mg/kg/day, 5 to about 15 mg/kg/day, or 5 to about 10 mg/kg/day.

5. A method for enhancing nitric oxide bioavailability in a subject in need thereof, wherein the subject has detectible nitric oxide deficiencies, associated with symptoms of acute respiratory distress syndrome (ARDS), or Severe Acute Respiratory Syndrome (SARS), and wherein the symptoms result from metastatic lung cancer or viral infections;

wherein the subject is administrated a composition comprising a symptom-reducing dose amount potassium nitrate, wherein the potassium nitrate, is administered with ascorbate, wherein the potassium nitrate and ascorbate is present in a weight ratio of 1 to 2, wherein the composition is water-soluble and is administered in the form of a capsule, tablet, lozenge, or chewable, wherein the composition is administered orally and wherein the composition increases salivary nitrite or salivary nitrite/nitrite within 90 minutes after consumption by the subject;

wherein the salivary nitrite or nitrite/nitrate is monitored with a dry-based Griess reagent test strip to determine a subsequent administration of nitrate, nitrate-ascorbate, or post-nitrate ascorbate dose;

wherein a second or intermittent dose is administered to the subject if subsequent salivary nitrite drops below <200 uM;

wherein the second dose is administered to sustain >300 uM salivary nitrite levels; wherein the second dose is usually administered within 4-10 hrs of the initial dose;

and wherein the intermittent dosing of two, but no more than three daily dosings per day, is administered to sustain >300 uM salivary nitrite throughout the day.

* * * * *